United States Patent [19]
Eykmann et al.

[11] Patent Number: 5,531,709
[45] Date of Patent: Jul. 2, 1996

[54] SYRINGE FOR THE CONTROLLED DISCHARGE OF VISCOUS MATERIALS

[75] Inventors: Rudolf Eykmann, Wehrheim; Joachim Fritze, Friedrichsdorf; Birgit Uhrig, Neu-Anspach; Dieter Schödel, Wiesbaden, all of Germany

[73] Assignee: Heraeus Kulzer GmbH, Wehrheim/Ts., Germany

[21] Appl. No.: 311,782

[22] Filed: Sep. 23, 1994

[30] Foreign Application Priority Data

Sep. 23, 1993 [DE] Germany ............................ 43 32 310.3

[51] Int. Cl.$^6$ .............................. A61M 5/315; A61C 5/04
[52] U.S. Cl. .......................... 604/218; 604/232; 604/235; 433/90
[58] Field of Search ..................... 604/232–235, 604/240, 275, 403, 415, 218; 433/89, 90; 222/570

[56] References Cited

U.S. PATENT DOCUMENTS

| 679,198 | 7/1901 | Witkowski | 604/232 |
|---|---|---|---|
| 4,472,141 | 9/1984 | Dragan | 604/232 |
| 5,002,538 | 3/1991 | Johnson | 604/240 |
| 5,171,214 | 12/1992 | Kolber et al. | 604/88 |

*Primary Examiner*—John D. Yasko
*Assistant Examiner*—Laird J. Knights
*Attorney, Agent, or Firm*—Webb Ziesenheim Bruening Logsdon Orkin & Hanson

[57] ABSTRACT

A syringe in which a discharge nozzle is connected to a cartridge of the syringe by ultrasonic welding. The discharge nozzle includes a triangular flow indicator configured to abut a triangular encircling groove located on the cartridge.

20 Claims, 2 Drawing Sheets

SYRINGE FOR THE CONTROLLED DISCHARGE OF VISCOUS MATERIALS

BACKGROUND OF THE INVENTION

1. Field of the Invention

This invention relates generally to a syringe for the controlled discharge of viscous materials and, more particularly, to a syringe for the controlled discharge of dental materials.

2. Description of the Prior Art

A syringe of the prior art is described, for example, in the product information published by Heraeus Kulzer GmbH "Charisma-Inlays—Gewinn durch Perfektion und Ästhetik" [Charisma Inlays—Profit from Perfection and Appearance] (31292/D 125 sK dt./WPR 12 12 200). These syringes, which contain the viscous dental materials sold under the name "Charisma" (Charisma is a registered trademark of Heraeus Kulzer GmbH), have a cartridge which holds the dental material. This cartridge is tapered on the outside circumference of its discharge end to form a material discharge nozzle which is closed by attaching a cap. In an end of the cartridge opposite the discharge end, a rotary piston is inserted. The rotary piston is in contact on one end with a sleeve-shaped stopper which is in contact with the viscous material in the cartridge. The rotary piston is provided with a threaded portion which is guided in a bearing in the form of a nut. To discharge the dental materials from the cartridge, the cap is removed from the cartridge and the rotary piston, which has a handle on its end, is twisted into the cartridge. The stopper is thus pushed toward the discharge end of the cartridge and applies pressure to the material. The syringes described above have been used successfully for years.

Another syringe for the discharge of viscous materials is disclosed in U.S. Pat. No. 3,581,399. This syringe has a removable tip or nozzle which is curved in the shape of a thin channel for controlled application of dental material to one spot on a tooth to be worked on. This tip is screwed onto the end of the cartridge or, in another embodiment, is swung into place and locked. German Application No. 42 00 044 A1 discloses a dental cartridge for the discharge of multi-component material for dental fillings which is inserted in a syringe and is operated by a lever. This syringe has a pistol-like adapter into which the cartridge containing the dental material is inserted. German GM 78 37 177 discloses a syringe for the direct application of dental filling material where the container which contains the filling material is configured as a collapsible capsule inserted into the cartridge. U.S. Pat. No. 3,900,954 discloses a syringe which is similar to the syringe disclosed in U.S. Pat. No. 3,581,399. A piston having a projecting tip is inserted under some friction into a cartridge. The tip of the piston presses into a sleeve-shaped part in which the dental material is located. The small, sleeve-shaped part is attached to the end of the cartridge and forms the discharge tip or nozzle for the material.

The cartridges described above which hold the dental materials are generally filled from the rear end, i.e., the end which is opposite the discharge nozzle. After the cartridge has been filled from the rear, the above-mentioned sleeve-shaped stopper is pushed into the open filling end of the cartridge until it is in contact with the loaded material. The rotary piston then presses against the stopper to discharge the material. Such cartridges which hold the dental material have a slight conicity on the inside, having a larger diameter on the side from which the dental material is filled and from which the stopper is inserted. The conicity is necessary for removing a workpiece after forming the cartridge by injection molding. Due to this conicity, the stopper is in contact with different tension in the axial direction of the cartridge against the inside wall of the cartridge as it moves from one end of the syringe to the other. There can be problems involving leaks in the cartridge, especially with low-viscosity materials. If a stopper is used which provides a tighter seal at the transition to the inside wall of the cartridge, after the process of filling the cartridge with material and insertion of the stopper, an air pocket remains between the material and the stopper which cannot escape. To counteract this problem, such stoppers were provided with a hole in the center and a drive spindle having a mandrel was provided to close the hole. After discharge of material from the cartridge, the pressure was removed from the stopper by retracting the rotary piston. However, if the rotary piston was twisted too far out of the syringe, the mandrel was necessarily pulled out of the hole in the stopper thus exposing the material in the cartridge to the atmosphere. This could result in a hardening of the material or a change in the characteristics of the material. It is precisely in the field of dentistry that very different materials must be inserted in such syringes or application instruments, including materials which polymerize when exposed to light or heat.

An object of the present invention is to design a syringe for the discharge of a controlled amount of viscous materials, in particular dental materials, which makes it possible to fill the syringe or its cartridges without the problem of an air pocket remaining between the dental material and the stopper, and which also makes possible a mechanical filling and closing of the cartridge.

SUMMARY OF THE INVENTION

A syringe of the present invention includes a material discharge nozzle which, at least on an end connected to a cartridge, is made of plastic. The discharge nozzle is fastened to the end of the cartridge on a connecting surface by ultrasonic welding.

The syringe or cartridge of the present invention is not filled, as is customary in the prior art, from the rear end, i.e., the end from which a rotary piston enters the cartridge, but rather from the front end, i.e., from the discharge end. The cartridge is sleeve-shaped and has an approximately uniform cross section over its length with a slight conicity at the discharge end. To fill the cartridge from the discharge end (the end which is opposite the end into which the rotary piston is inserted), the stopper is inserted into the cartridge and pushed slightly into the cartridge. Then, as the materials are being injected, if necessary up to a stop on the cartridge, the stopper is displaced to the rear. This displacement is caused by the material in contact with the stopper. Therefore, there is no air pocket between the stopper and the material since from the beginning of the filling process the air can be expelled from the cartridge. After the cartridge has been filled, an end of the cartridge having a connecting surface is connected to a material discharge nozzle by ultrasonic welding. This ultrasonic welding has the advantage that the sound waves can be targeted at the vicinity of the connection between connecting surfaces of the cartridge or of the discharge nozzle, so that the sound waves are converted into heat only at this location. Consequently, no heat is transmitted to the dental material in the cartridge. Such filling of the cartridges with material and subsequent closing by means of ultrasonic welding can be performed mechanically.

An additional advantage is that the ultrasound waves are barely audible and thus do not cause any disruptive noise in the vicinity of the filling machine. Such an ultrasonic welding can be performed in the frequency range from 20 to 40 kHz, but preference is given to the higher frequency range. In this high frequency range, an output of the welding head between 350 and 700 watts can be used.

The discharge nozzle to be connected to the cartridge and the cartridge itself are preferably made of polypropylene. The connecting surface of the material discharge nozzle is preferably oriented parallel to the end surface of the cartridge. This guarantees that the sound waves can be applied in a uniform distribution around the circumference of the cartridge. If this nozzle connecting surface projects slightly beyond the outside circumference of the cartridge, the connecting surface is at a sufficient distance during the ultrasonic welding to prevent damage to the material in the cartridge. It also makes possible a proper cooling of the weld seam after ultrasonic welding since the heat is discharged outwardly. To target the ultrasound energy in the vicinity of the connecting surface of the material discharge nozzle, one configuration of the invention includes an encircling raised portion formed on the connecting surface of the material discharge nozzle, and which forms an indicator of the energy flow. This energy flow indicator preferably tapers toward a point at a free end. The ultrasonic energy is applied to this energy flow indicator, preferably to its free end or tip so that this energy flow indicator is heated from the tip. The thermoplastic material of the flow indicator flows and is connected to the cartridge. During this process, the cartridge and the material discharge nozzle are held together under pressure.

As mentioned above, the material discharge nozzle should have an encircling edge which projects beyond the nozzle connecting surface, and which is in contact with the outside of the cartridge. In addition to providing for a good discharge of heat, this design also forms a large sealing surface having one segment extending toward the wall of the cartridge and another shorter segment extending in the longitudinal direction of the cartridge in the vicinity of the projecting edge of the discharge nozzle. The above-mentioned energy flow indicator is located in the transitional area between the connecting surface and the projecting edge.

On the outside of the material discharge nozzle there is an outer surface (connecting surface) which runs approximately parallel to the connecting surface on the cartridge. To correctly orient an ultrasonic welding head with respect to the connecting surface during the ultrasonic welding, the ultrasound head is applied to this outer surface.

Additional details and features of the invention are explained in the following description of the invention which is illustrated in the accompanying drawings.

DESCRIPTION OF THE PREFERRED EMBODIMENTS

Figure 1:
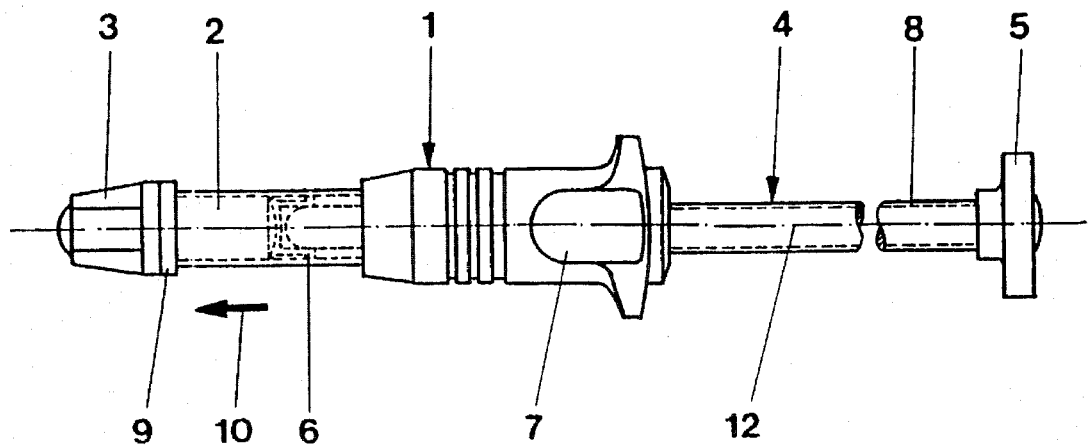
FIG. 1 is a lateral plan view of a syringe with an adapter and a cartridge inserted therein in accordance with the present invention.

As shown in FIG. 1, a syringe for the controlled discharge of materials, in particular pasty materials, includes an adapter 1 in which is held a cartridge 2 closed by a cap 3 on a free end which projects out of the adapter 1. The cartridge 2 is filled with a material to be discharged and worked. A rotary piston 4 having a handle 5 on a free end enters the adapter 1 on the end opposite the cartridge 2. The inserted end of the rotary piston 4 presses against a stopper 6, which is indicated by broken lines in FIG. 1. The rotary piston 4 is held in the adapter part 1 in a bearing 7 into which the rotary piston 4 is screwed by means of a threaded portion 8. To discharge material from the cartridge 2 via the discharge nozzle 9, as shown in various embodiments in FIGS. 2 to 5, the rotary piston 4 is rotated by the handle 5 and the stopper 6 is advanced in the direction indicated by the arrow 10 in FIG. 1 and presses against the material contained in the cartridge 2. After use, the rotary piston 4 is twisted slightly back, so that the pressure is removed from the stopper 6 and the closing part or the cap 3 is replaced on the discharge nozzle 9.

Depending on the type of dental materials contained in the cartridge 2 and on the specific purpose of the application, different shapes of discharge nozzles 9 may be attached to the cartridge 2. For this purpose, various embodiments of the discharge nozzle 9, like those illustrated in FIGS. 2 to 5, can be connected to the cartridge 2.

The discharge nozzle 9 is connected to the cartridge 2 by means of ultrasonic welding. For this purpose, connecting surfaces 11a and 11b between the cartridge 2 and the discharge nozzle 9 are preferably planar and run parallel to one another. These connecting surfaces 11a and 11b run perpendicular to the axis 12 of the cartridge 2 and the discharge nozzle 9. The cartridge 2 has a projecting edge 13 which projects outward, in particular to enlarge connecting surface 11a of the cartridge 2. The discharge nozzle 9 has an encircling edge 14 running around the circumference of the nozzle connecting surface 11b, which projects beyond the plane of the connecting surface 11b. The inside diameter of the area which is surrounded by the encircling edge 14 approximately equals the outside circumference of the cartridge 2 in the vicinity of the projecting edge 13, so that when the cartridge 2 and the discharge nozzle 9 are assembled, the encircling edge 14 externally surrounds the cartridge projecting edge 13. On connecting surface 11b of the discharge nozzle 9, there is an encircling projection or energy flow indicator 15 which preferably has a triangular cross section as shown in FIGS. 3 and 4.

Figure 4:
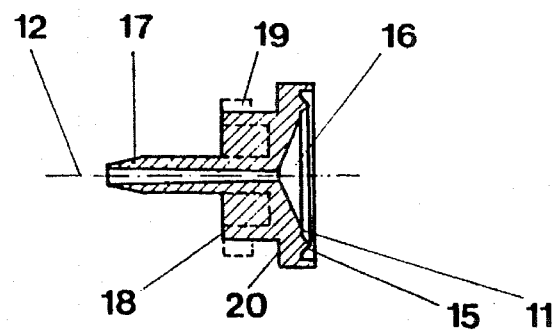
Figure 5:
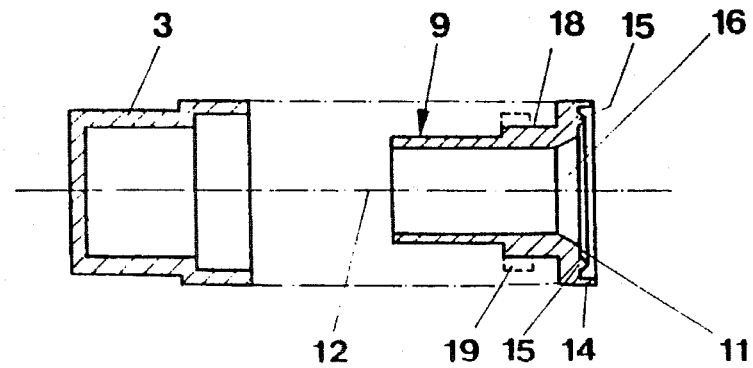
FIG. 5 is a section through a discharge nozzle closed by a cap.

The individual discharge nozzles 9 each have an enlarged entrance area 16 which is funnel-shaped and which on one end matches the inside diameter of the cartridge 2 and on the other end matches the inside diameter of the discharge tip 17. On the outside of each of the various discharge nozzles 9 illustrated in FIGS. 2 to 5, there is a shoulder area 18 in the form of a cylindrical segment which, in the individual embodiments of the discharge nozzles with different sized discharge tips 17, always has the same outside diameter and the same axial length. As shown in FIG. 1, an identical cap 3 can be placed on this shoulder area 18 of the various discharge nozzles 9. This cap-shaped closing part 3 can be locked on projections 19 which are shown in FIGS. 3, 4 and 5 by means of grooves and slots (not shown) in the cap 3.

Figure 2:
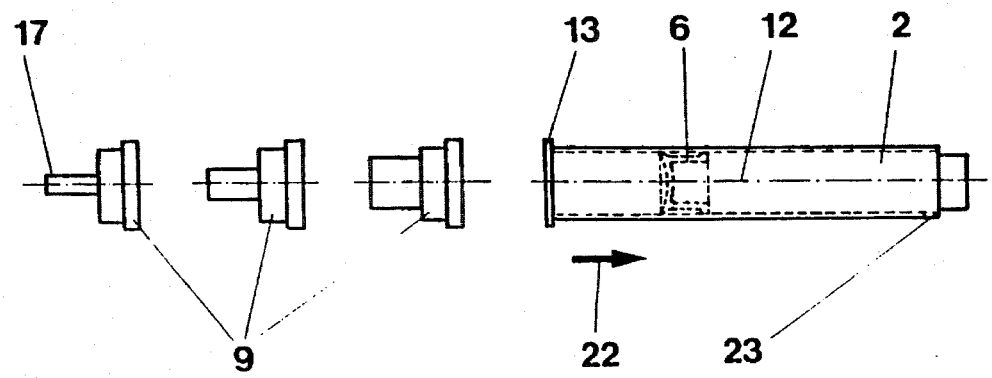
FIG. 2 is a lateral plan view of a cartridge with various discharge nozzles.
Figure 3:
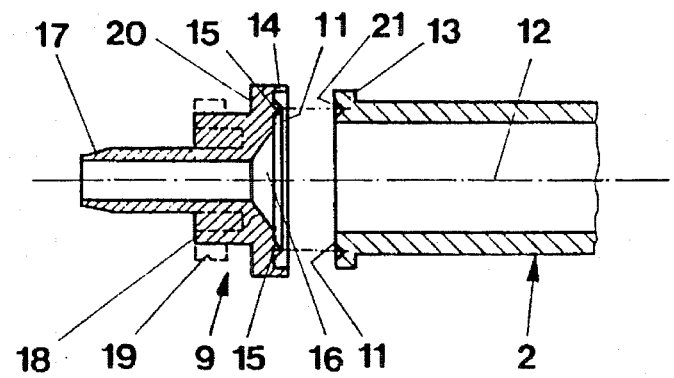
FIGS. 3 and 4 are sectional view of two discharge nozzles on an enlarged scale.

To connect the two plastic parts to one another, i.e., the cartridge 2 and the discharge nozzle 9, the two parts are oriented in relation to one another as shown in FIGS. 2 and 3 and their connecting surfaces 11a and 11b are placed together. The two connecting surfaces 11a and 11b of the discharge nozzle 9 on the one hand and of the cartridge 2 on the other hand are, in this position, held at a distance from one another by the energy flow indicator 15 which contacts the connecting surface 11a of the cartridge 2. In this position, an ultrasonic welding head is placed on the outside of the discharge nozzle 9, parallel to the connecting surfaces 11a and 11b. The individual discharge nozzles 9 are provided with a connecting surface 20 which is formed by the end surface of a cylindrical segment of the discharge nozzle 9, the diameter of which is greater than the diameter of the cylindrical shoulder area. By means of this connecting surface 20, ultrasonic energy, i.e., ultrasound at a frequency between 20 to 40 kHz and a power of approximately 350 to 700 watts, can be applied in a controlled manner to the tip of the energy flow indicator 15 which is thereby heated and flows so that the two parts are joined to one another at their connecting surfaces 11a and 11b by means of the softened or liquefied plastic. To further improve the connection between the two parts and to enlarge connecting surface 11a, an encircling groove 21 can be provided in the connecting surface 11a of the cartridge 2, as shown in FIG. 3. The encircling groove 21 has a triangular cross section similar in cross section to that of the energy flow indicator 15. However, this encircling groove 21 is sized so that its cross section is somewhat smaller than the cross section of the energy flow indicator 15 so that no cavities will remain when the two parts are welded to one another.

Preferably, the discharge nozzle 9 and/or the cartridge 2 are made of polypropylene. This material is preferred because it has good welding properties and is not a good conductor of heat. The strength of the weld seam is approximately equal to the inherent strength of the material. The welding process does not take a long time, and the material is not exposed to any harmful effects.

The syringe or cartridge 2 which is closed by the discharge nozzle 9 has the advantage that it can be filled with material by the manufacturer from the front, i.e., from the end which is attached to the discharge nozzle 9. To fill the cartridge, first the stopper 6 is placed in the empty cartridge 2 and is in tight contact against the inside wall of the cartridge 2. Then the cartridge is inserted in a charging station and the material is injected into the cartridge 2, whereupon the stopper 6 is pushed toward the rear end of the cartridge 2 in the direction indicated by the arrow 22 in FIG. 2 until the stopper contacts a stop area 23 with a smaller diameter than that of the stopper. During this filling process, no air pockets are left in the vicinity of the stopper 6 since the air which is in front of the stopper 6 is forced out of the cartridge 2 at the beginning of the process of filling the cartridge 2 with material. Then the filled cartridge 2 is inserted in an ultrasonic welding device and welded to the discharge nozzle 9. The ultrasonic welding has the advantage that only the encircling projection or energy flow indicator 15 on the connecting surface 11b of the discharge nozzle 9 is heated. The material which has already been loaded into the cartridge 2 is not exposed to any heating and is in no way affected by the ultrasonic welding process.

While embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention which is to be given the full breadth of the appended claims and any and all equivalents thereof.

What is claimed is:

1. A syringe for the controlled discharge of viscous materials for use in dental applications, said syringe comprising:

a cartridge for holding the dental viscous material;

a stopper mounted within said cartridge;

a rotary piston configured to be inserted into one end of said cartridge;

a bearing holding said piston; and a material discharge nozzle located at another end of said cartridge, wherein said discharge nozzle includes an opening at a discharge end thereof having a width which is smaller than an inside diameter of said cartridge, wherein said rotary piston includes an insertion end pressing against said stopper, wherein said rotary piston is movably held in said bearing, wherein at least an end of said material discharge nozzle which is connected to said cartridge is made of plastic, and wherein a connecting surface of said discharge nozzle is fastened by means of ultrasonic welding to an end of said cartridge to a connecting surface of said cartridge, and wherein one said connecting surface includes an elevation extending away therefrom which forms an indicator of energy flow.

2. A syringe as claimed in claim 1, wherein said connecting surface of said material discharge nozzle runs parallel to an end surface of said cartridge.

3. A syringe for the controlled discharge of viscous materials, said syringe comprising:

a cartridge for holding the viscous material;

a stopper mounted within said cartridge;

a rotary piston configured to be inserted into one end of said cartridge;

a bearing holding said piston; and a material discharge nozzle located at one end of said cartridge, wherein said discharge nozzle includes an opening at a discharge end thereof having a width which is smaller than an inside diameter of said cartridge, wherein said rotary piston includes an insertion end pressing against said stopper, wherein said rotary piston is movably held in said bearing, wherein at least an end of said material discharge nozzle which is connected to said cartridge is made of plastic, and wherein said discharge nozzle is fastened by means of ultrasonic welding to an end of said cartridge on a connecting surface of said discharge nozzle;

wherein on said connecting surface of said material discharge nozzle, there is a raised, encircling portion which forms an indicator of energy flow.

4. A syringe as claimed in claim 3, wherein said indicator of energy flow tapers to a point on a free end.

5. A syringe as claimed in claim 1, wherein said material discharge nozzle includes an encircling edge projecting beyond said connecting surface and which is in contact with an outside of said cartridge.

6. A syringe as claimed in claim 3, wherein said indicator of energy flow is located in a transitional region between said connecting surface and an encircling edge.

7. A syringe as claimed in claim 1, wherein said material discharge nozzle includes a connecting surface which is approximately parallel to a connecting surface of said cartridge.

8. A syringe as claimed in claim 1, wherein said cartridge and said material discharge nozzle are made of polypropylene.

9. A syringe as claimed in claim 2, wherein said connecting surface of said material discharge nozzle includes a raised, encircling portion which forms an indicator of energy flow.

10. A syringe as claimed in claim 9, wherein said indicator of energy flow tapers to a point on a free end.

11. A syringe as claimed in claim 2, wherein said material discharge nozzle includes an encircling edge projecting beyond said connecting surface and configured to contact an outside of said cartridge.

12. A syringe as claimed in claim 3, wherein said material discharge nozzle includes an encircling edge projecting beyond said connecting surface and configured to contact an outside of said cartridge.

13. A syringe as claimed in claim 4, wherein said material discharge nozzle includes an encircling edge projecting beyond said connecting surface and configured to contact an outside of said cartridge.

14. A syringe for the controlled discharge of viscous materials, said syringe comprising:

a cartridge for holding the viscous material;

a stopper mounted within said cartridge;

a rotary piston configured to be inserted into one end of said cartridge;

a bearing holding said piston; and a material discharge nozzle located at another end of said cartridge, wherein said discharge nozzle includes an opening at a discharge end thereof having a width which is smaller than an inside diameter of said cartridge, wherein said rotary piston includes an insertion end pressing against said stopper, wherein said rotary piston is movably held in said bearing, wherein at least one end of said material discharge nozzle which is connected to said cartridge is made of plastic, and wherein said discharge nozzle is fastened by means of ultrasonic welding to an end of said cartridge on a connecting surface of said discharge nozzle;

wherein said cartridge includes a connecting surface having an encircling groove disposed thereon.

15. A syringe as claimed in claim 3, wherein said cartridge includes a connecting surface having an encircling groove disposed thereon and wherein said encircling groove has a cross section similar to a cross section of said encircling portion.

16. A syringe as claimed in claim 15, wherein a cross-sectional area of said groove is less than a cross-sectional area of said encircling portion.

17. A syringe for controlling discharge of viscous materials, said syringe comprising:

a hollow, cylindrical cartridge for holding the viscous material, said cartridge having a first end and opposed second end, an opening at said second end having a diameter equal to an inner diameter of a cylindrical interior of said cartridge, and a connecting surface at said second end;

a stopper movably positioned within said interior of said cartridge;

a piston receivable within said cartridge adapted to engage with and move said stopper; and a discharge nozzle having an opening at a first end thereof having a diameter smaller than said diameter of said opening at said second end of said cartridge, said discharge nozzle including a plastic connecting surface at a second end thereof which is attached by ultrasonic welding to said connecting surface of said second end of said cartridge.

18. The syringe of claim 17, wherein said nozzle has an opening at a second end thereof which has a diameter equal to said diameter of said opening at said second end of said cartridge which is equal to said inner diameter of said interior of said cartridge.

19. The syringe of claim 17, wherein said cartridge includes a projecting edge at said second end thereof extending radially outward from said opening at said second end of said cartridge, said projecting edge having said connecting surface of said cartridge on one end thereof;

wherein said nozzle includes a flange at said second end thereof extending radially outward from said opening of said second end of said cartridge, said flange having said connecting surface of said nozzle on one end thereof.

20. The syringe of claim 19, further including an encircling edge on said nozzle extending from said connecting surface of said nozzle, said encircling edge surrounding said projecting edge of said cartridge.

\* \* \* \* \*